United States Patent [19]

Hoffmann et al.

[11] 4,143,065

[45] Mar. 6, 1979

[54] POLYCYCLIC SCENTS

[75] Inventors: Werner Hoffmann, Neuhofen; Karl Von Fraunberg, Bobenheim, both of Fed. Rep. of Germany

[73] Assignee: BASF Aktiengesellschaft, Rheinland, Pfalz, Fed. Rep. of Germany

[21] Appl. No.: 815,931

[22] Filed: Jul. 15, 1977

Related U.S. Application Data

[62] Division of Ser. No. 708,994, Jul. 26, 1976, Pat. No. 4,076,748.

[51] Int. Cl.$^2$ ............................................. C07C 121/48
[52] U.S. Cl. .................................... 260/464; 131/144; 252/89 R; 252/174; 252/522; 426/538
[58] Field of Search .......................... 252/522; 260/464

[56] References Cited

U.S. PATENT DOCUMENTS

| 2,217,632 | 10/1940 | Wolfe | 260/464 |
| 2,771,470 | 11/1956 | Mark | 260/464 X |
| 3,714,220 | 1/1973 | Dahill, Jr. | 252/522 X |
| 3,920,585 | 11/1975 | Klein | 252/522 |
| 3,928,247 | 12/1975 | Mookherjee et al. | 252/522 |
| 3,960,920 | 6/1976 | Ohotsubo | 260/464 |
| 3,992,433 | 11/1976 | Ariyoshi et al. | 260/464 X |

Primary Examiner—Joseph Paul Brust
Attorney, Agent, or Firm—Keil, Thompson & Shurteleff

[57] ABSTRACT

New polycyclic Diels-Alder adducts which are formed on reaction of 8-vinyl-tricyclo-[5,2,1,0$^{2,6}$]-dec-8-ene or 8-hydroxy-8-vinyl-tricyclo-[5,2,1,0$^{2,6}$]-decane with alkenes or alkynes having one or two activating substituents, e.g., —COOH, —COOCH$_3$, —COOC$_2$H$_5$, —CHO, —COCH$_3$, —COC$_2$H$_5$ or —CN. They have green, fresh, fruity and in some cases woody odors with long-lasting tenacity and/or fixing properties. They can be used as constituents of perfumes and of compositions for perfuming body care products, detergents and other consumer products.

2 Claims, No Drawings

POLYCYCLIC SCENTS

The subject application is a divisional application of Ser. No. 708,994, which was filed in the U.S. on July 26, 1976 and is now allowed and is U.S. Pat. No. 4,076,748 issued Feb. 28, 1978.

The present invention relates to Diels-Alder adducts of the general formula I

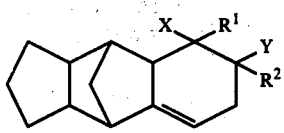

where $R^1$ and $R^2$ are —H or —$CH_3$, or $R^1$ and $R^2$ together are a further bond between the carbon atoms on which they are present, and X and Y are each —$CH_2OH$, —CH(OH)—$CH_3$, —COOH, —$COOCH_3$, —$COOC_2H_5$, —CHO, —CO—$CH_3$, —CO—$C_2H_5$ or —CN, or X and Y together are —CO—O—CO—, or one of X or Y is —H or $CH_3$ and the other has one of the above meanings.

The new polycyclic Diels-Alder adducts are distinguished by valuable scent characteristics. They have green, fresh, fruity and in some cases woody odors with long-lasting tenacity and/or fixing properties. They may be used as constituents of perfumes and of compositions for perfuming body care products, e.g. soaps, shampoos and hair lotions, detergents and other consumer products. Furthermore, they may be used for flavoring foodstuffs and tobacco.

The present invention further relates to a process for the manufacture of the new compounds of the formula I, wherein the new 8-vinyltricyclo-[5,2,1,0$^{2,6}$]-dec-8-ene of the formula II

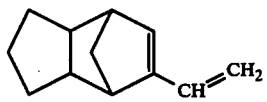

is subjected to a Diels-Alder reaction, by conventional methods, with a dienophile of the general formula III

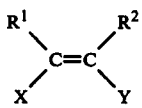

where $R^1$ and $R^2$ are —H or —$CH_3$ or $R^1$ and $R^2$ together are a further bond between the carbon atoms on which they are present and X and Y are each —COOH, —$COOCH_3$, —$COOC_2H_5$, —CHO, —$COCH_3$, —$COC_2H_5$ or —CN, or X and Y together are —CO—O—CO—, or one of X and Y is —H or —$CH_3$ and the other has one of the above meanings.

The new Diels-Alder adducts of the formula I, in which $R^1$ and $R^2$ are —H or —$CH_3$ and one of X or Y is —$CH_2OH$ or —CH(OH)—$CH_3$ and the other is H, are obtained by reducing the corresponding oxo compounds by conventional methods.

8-Vinyl-tricyclo-[5,2,1,0$^{2,6}$]-dec-8-ene, required as a starting compound, can be manufactured by a simple conventional method, by elimination of water from 8-vinyl-tricyclo-[5,2,1,0$^{2,6}$]-decan-8-ol, which in turn can be obtained by reacting tricyclo-[5,2,1,0$^{2,6}$]-decan-8-one, which is readily accessible, with a vinyl-magnesium halide by the Grignard method. Instead of the diene II, 8-vinyl-tricyclo-[5,2,1,0$^{2,6}$]-decan-8-ol can be used as the starting material, but this requires more severe reaction conditions, e.g. higher temperatures and/or acid catalysts, and the yields are therefore frequently less.

Suitable dienophiles of the formula III are:

(a) Alkenes having only one activating substituent, i.e. compounds of the formula III, where $R^1$ and $R^2$ are —H or —$CH_3$, one of X or Y is —COOH, —$COOCH_3$, —$COOC_2H_5$, —CHO, —CO—$CH_3$, —CO—$C_2H_5$ or —CN and the other X or Y is —H, i.e. mono-$\alpha,\beta$-unsaturated aldehydes, ketones, nitriles, carboxylic acids or carboxylic acid esters. Examples which may be mentioned are acrolein, methacrolein, crotonaldehyde, methyl vinyl ketone, pent-2-en-4-one, acrylonitrile, methacrylonitrile, crotononitrile, acrylic acid, methacrylic acid, crotonic acid and the methyl esters and ethyl esters of the said 3 acids. The above aldehydes, ketones and nitriles are preferred.

(b) Alkenes with two activating substituents, i.e. compounds of the formula III, where $R^1$ and $R^2$ are —H or —$CH_3$, especially —H, and X and Y are each —COOH, —$COOCH_3$, —$COOC_2H_5$, —CHO, —CO—$CH_3$, —CO—$C_2H_5$ or —CN, or X and Y together are —CO—O—CO—. Examples which may be mentioned are dimethyl fumarate, diethyl fumarate and maleic anhydride.

(c) Alkylenes with only one activating substituent, i.e. compounds of the formula III, where $R^1$ and $R^2$ together are a further bond between the carbon atoms on which they are present, one of X or Y is —COOH, —$COOCH_3$, —$COOC_2H_5$, —CHO, —CO—$CH_3$, —CO—$C_2H_5$ or —CN and the other is —H or —$CH_3$. Examples which may be mentioned are propionaldehyde (propynal), butyn-2-al, propionic acid, tetrolic acid (butyn-2-oic acid), and the methyl esters and ethyl esters of the said acids.

(d) Alkynes with two activating substituents, i.e. compounds of the formula III, where $R^1$ and $R^2$ together are a further bond between the carbon atoms on which they are present and X and Y are each —COOH, —$COOCH_3$, —$COOC_2H_5$, —CHO, —CO—$CH_3$, —CO—$C_2H_5$ or —CN. Examples which may be mentioned are acetylenedicarboxylic acid and its methyl and ethyl esters.

The dienophiles of the formula III are, in general, known and commercial compounds.

Preferably, the alkenes with only one actuating substituent, described under (a), are used as dienophiles of the formula III.

In general, the Diels-Alder reaction is carried out by bringing a mixture of 8-vinyl-tricyclo-[5,2,1,0$^{2,6}$]-dec-8-ene (II), the dienophile of the formula III and, if appropriate, an inert solvent, to from 0 to 150° C., preferably from 30 to 80° C., for the length of the reaction time. The latter is from about 1 to 200 hours, depending on the nature of the dienophile. The dienophile is in general used in from about 0.5 to 10 molar amount, preferably in from about 2 to 5 molar amount, based on II.

To avoid possible resinification reactions, a small amount, i.e. from about 10 to 100 mg per mole of II, of a conventional stabilizer for Diels-Alder reactions, e.g. hydroquinone, is generally added to the reaction mixture.

The reaction may be carried out in the absence of solvents or in an inert solvent.

Examples of inert solvents which can be used are aliphatic hydrocarbons, e.g. pentane, hexane, cyclohexane and hydrocarbon fractions, aromatic hydrocarbons, e.g. benzene, toluene or xylene, chlorohydrocarbons, e.g. methylene chloride, chloroform or chlorobenzene, ethers, e.g. diethyl ether, dipropyl ether, diisopropyl ether, tetrahydrofuran and anisole, alcohols, e.g. methanol, ethanol, propanol, isopropanol and cyclohexanol, ketones, e.g. acetone, methyl ethyl ketone and methyl isopropyl ketone, amides, e.g. dimethylformamide, dimethylacetamide and hexamethylphosphotriamide or nitro compounds, e.g. nitromethane and nitrobenzene, or mixtures of the said solvents.

The reaction is either carried out at atmospheric pressure or under the autogenic pressure of the reactants in closed reaction vessels.

The reaction mixture is worked up by conventional methods, e.g. by distillation.

Regarding further details of Diels-Alder reactions, reference may be made to R. Sauer, Angew. Chem. 79 (1967), 77–94.

The Diels-Alder adducts are in general obtained as mixtures of different isomers. When using unsymmetrical olefins of the formula III, 8 stereoisomeric Diels-Alder adducts are possible, depending on the steric course of the addition reaction. The dienophile can attack "meta" or "ortho" to the $C_9$ of the diene of the formula II, "exo" or "endo" and from above or from below. The general rules of the Diels-Alder reaction and analogous examples with vinyl cyclohexenes or vinyl-bicylenes (see A. S. Onishchenko "Diene Synthesis", Israel Program for Scientific Translation, Jerusalem 1964, pages 410–445, especially pages 410–413 and pages 423–425) lead to the expectation that the main product would be the "ortho-endo" isomer, i.e. in the case of acrolein the isomers

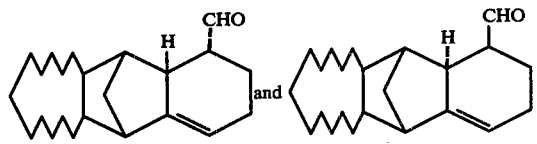

with the attack "from below" in the former case and "from above" in the latter. A prediction of the actual attack is difficult, given the complicated stereochemistry of the diene, and is decisively dependent on the exo/endo configuration of the 5-membered ring. If symmetrical olefins and alkynes are used as dienophiles of the formula III, the number of possible stereoisomers is less.

The stereoselectivity of the reaction can be increased by using very low reaction temperatures and/or by adding catalytic amounts of Lewis acids, e.g. $BF_3$, $AlCl_3$, $ZnCl_2$ and the like (l.c., especially page 84).

If the reaction is carried out in the presence of catalytic amounts of a Lewis acid such as $AlCl_3$, $BF_3$, $SnCl_4$ or $ZnCl_2$, the procedure followed is that described above, but at lower temperatures, i.e. at from about −80 to +20° C., preferably from −40 to 0° C.

The amount of catalyst is from 0.1 to 10%, preferably from 0.5 to 5%, based on II employed.

Carbonyl compounds can be reduced to the alcohols in accordance with numerous standard processes, e.g. by catalytic hydrogenation, by reduction with metals or metal hydrides or by electrochemical or photochemical reduction. Regarding further details, reference may be made to S. Patai, "The Chemistry of the Hydroxyl Group", Interscience Publishers 1971, pages 231–243. Example 3 describes the reduction of a carbonyl compound with a metal hydride ($NaBH_4$).

The new polycyclic Diels-Alder adducts are distinguished by valuable scent properties. They have green, fresh, fruity and in some cases woody scents with long-lasting tenacity. Furthermore, they possess fixing properties. Accordingly, they can be used as constituents of perfumes and of compositions for perfuming body care products, e.g. soaps, shampoos and hair lotions, detergents and other consumer products. The scent depends somewhat on the stereochemistry (exo/endo ratio) of the tricyclo-$[5,2,1,0^{2,6}]$-decan-8-one employed, but in general it is satisfactory to use the adducts obtained from the commercial ketone.

EXAMPLE

A solution of 8.0 g (0.05 mole) of 8-vinyl-tricyclo-$[5,2,1,0^{2,6}]$-dec-8-ene, 10.6 g (0.2 mole) of acrylonitrile, 50 ml of toluene and 10 mg of hydroquinone is heated at 80° C. for 12 hours. The reaction mixture is then cooled, washed with twice 30 ml of water, concentrated and distilled. 8.1 g (corresponding to 76% of theory) of an 80 : 20 mixture of nitriles pass over at from 125 to 128° C./0.2 mm Hg. From the analytical and spectroscopic data, the main product probably has the formula I, where $R^1$, $R^2$ and Y are —H and X is —CN.

$n_D^{25}$: 1.5325.

Scent: fresh, flowery, slightly fruity (lime), good tenacity.

What we claim is:

1. A Diels-Alder adduct of the general formula I

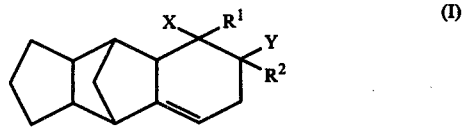

where $R^1$ and $R^2$ are independently —H or —$CH_3$, or $R^1$ and $R^2$ together are a further bond between the carbon atoms on which they are present, and X and Y are each independently —CN or one of X and Y is —H or —$CH_3$ and the other has the above meaning.

2. A Diels-Alder adduct of the general formula I

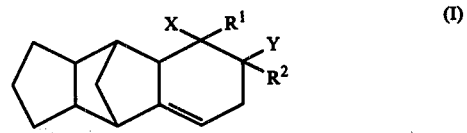

where $R^1$ and $R^2$ are independently —H or —$CH_3$, one of X and Y is —CN and the other is —H.

* * * * *

UNITED STATES PATENT AND TRADEMARK OFFICE
CERTIFICATE OF CORRECTION

PATENT NO. : 4,143,065
DATED : March 6, 1979
INVENTOR(S) : Werner Hoffmann et al It is certified that error appears in the above-identified patent and that said Letters Patent are hereby corrected as shown below:

Please add:

-- [30] Foreign Application Priority Data

Sept. 1, 1975 Germany.......... 25 38 790 ---

Signed and Sealed this

Twenty-second Day of January 1980

[SEAL]

Attest:

SIDNEY A. DIAMOND

Attesting Officer      Commissioner of Patents and Trademarks